United States Patent [19]

Furukawa et al.

[11] Patent Number: 5,149,831
[45] Date of Patent: Sep. 22, 1992

[54] PROCESS FOR PRODUCING METHYLNORBORNENE DICARBOXYLIC ACID ANHYDRIDE

[75] Inventors: Hiroshi Furukawa, Kawagoe; Hiroyuki Inagaki, Saitama; Masaharu Ishii, Saitama; Hiroshi Ueno, Saitama, all of Japan

[73] Assignee: Tonen Corporation, Tokyo, Japan

[21] Appl. No.: 671,574

[22] Filed: Mar. 19, 1991

[30] Foreign Application Priority Data

Apr. 27, 1990 [JP] Japan .................................. 2-110586

[51] Int. Cl.$^5$ .......................................... C07D 307/77
[52] U.S. Cl. ..................... 549/237; 549/236
[58] Field of Search ................................ 549/236, 237

[56] References Cited

U.S. PATENT DOCUMENTS 1,944,731  1/1934  Diels et al. .......................... 549/237

OTHER PUBLICATIONS

Sauer, Angew, Chem. Int. Edit. vol. 6, 16, 1967.

*Primary Examiner*—Nicholas S. Rizzo
*Assistant Examiner*—Y. N. Gupta

[57] ABSTRACT

Methylnorbornene dicarboxylic anhydride is produced from a $C_6$-$C_7$ fraction containing 5-methylcyclopentadiene by carrying out the reaction in the presence of a maleic anhydride and a protonic acid at a temperature of 0°-50°C., whereby the 5-methylcyclopentadiene is isomerized to 1-MCPD and 2-MCPD which undergo a Diels-Alder reaction to form methylnorbornene dicarboxylic anhydride.

5 Claims, No Drawings

PROCESS FOR PRODUCING METHYLNORBORNENE DICARBOXYLIC ACID ANHYDRIDE

The present invention relates to a process for producing methylnorbornene dicarboxylic acid anhydride. More particularly, it is concerned with a process for producing methylnorbornene dicarboxylic acid anhydride through Diels-Alder reaction in the presence of a specific catalyst at a specific reaction temperature, from a hydrocarbon fraction (which is a $C_{6-7}$ fraction of naphtha steam cracking, containing diolefins such as methylcyclopentadiene) and maleic anhydride.

It is known that an alicyclic dicarboxylic acid anhydride is used as a hardener for epoxy resins. In fact, methylnorbornene dicarboxylic acid anhydride, which is liquid at room temperature, is in general use as a hardener for epoxy resins which need heat resistance. Its manufacturing method is described in Japanese Patent Publication No. 28504/1982.

Unfortunately, the above-mentioned methylnorbornene dicarboxylic acid anhydride has a disadvantage of high production cost, because it is usually produced by converting methylcyclopentadiene dimer (which is expensive) into methylcyclopentadiene (MCPD) by thermal decomposition and adding MCPD to maleic anhydride by DielsAlder reaction.

The production cost would be reduced if it is possible to produce methylnorbornene dicarboxylic acid anhydride through Diels-Alder reaction between a hydrocarbon fraction (which is a $C_{6-7}$ fraction resulting from steam cracking of a hydrocarbon mixture such as naphtha, and containing diolefins such as MCPD) and maleic anhydride. This process, however, has the following problems.

The fraction resulting from steam cracking usually contains MCPD which is a mixture of three structural isomers, namely, 1-methylcyclopentadiene (1-MCPD), 2-methylcyclopentadiene (2-MCPD), and 5-methylcyclopentadiene (5-MCPD), which are shown in the following formulae.

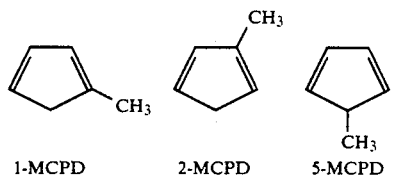

1-MCPD   2-MCPD   5-MCPD

1-MCPD and 2-MCPD readily react with maleic anhydride, but 5-MCPD does not react with maleic anhydride because of its steric hindrance if Diels-Alder reaction is carried out at 20°-35° C. so that heavy substances are formed in only small quantities. Therefore, the yield of methylnorbornene dicarboxylic acid anhydride is very low relative to the amount of MCPD.

On the other hand, Diels-Alder reaction at 75°-85° C., which is high enough for 5-MCPD to react with maleic anhydride, gives rise to heavy substances, reducing the yield, and also gives rise to methylnorbornene dicarboxylic acid anhydride having a low purity because of the side reactions of diolefins (other than MCPD contained in the fraction) with maleic anhydride.

The present invention was completed to address the above-mentioned problems encountered in the prior art technology. Accordingly, it is an object of the present invention to provide a process for producing methyl norbornene dicarboxylic acid anhydride of high purity in a high yield at a low production cost.

In the course of investigation on the process for producing methylnorbornene dicarboxylic acid anhydride at a low production cost, the present inventors noticed that the $C_{6-7}$ fraction resulting from steam cracking of a hydrocarbon mixture such as naphtha contains MCPD in an amount of 3.0-8.0 wt. %, and found that it is possible to produce methylnorbornene dicarboxylic acid anhydride of high purity in a high yield from the fraction (without purification) and maleic anhydride through Diels-Alder reaction which is performed at a specific temperature in the presence of a specific catalyst. This finding led to the present invention.

Accordingly, the present invention relates to a process for producing methylnorbornene dicarboxylic acid anhydride by reacting a mixture containing diolefins (such as MCPD) with maleic anhydride, characterized in that the reaction is carried out at 0°-50° C. in the presence of a protonic acid. The mixture is a $C_{6-7}$ hydrocarbon fraction which is produced when a hydrocarbon mixture such as naphtha undergoes thermal decomposition in the presence of steam.

The following is the detailed description of the process for producing methylnorbornene dicarboxylic acid anhydride according to the present invention.

According to the process of the present invention, methylnorbornene dicarboxylic acid anhydride is produced from a $C_{6-7}$ hydrocarbon fraction containing diolefins such as MCPD which is obtained by steam cracking of a hydrocarbon mixture such as naphtha. This hydro-carbon fraction usually has the following composition.

| | |
|---|---|
| 1-MCPD | 0.7–2.0 wt. % |
| 2-MCPD | 0.8–2.0 wt. % |
| 5-MCPD | 1.5–4.0 wt. % |
| 1,3-cyclohexadiene | 0.5–1.0 wt. % |
| 1,3-hexadiene | 0.2–1.0 wt. % |
| 2-ethyl-1,3-butadiene | 0.3–1.0 wt. % |
| $C_{6-7}$ olefin or paraffin | 4.5–8.5 wt. % |
| Benzene | 40–60 wt. % |
| Toluene | 20–40 wt. % |

According to the process of the present invention, the hydrocarbon fraction having the above-mentioned composition undergoes Diels-Alder reaction without purification for the production of methylnorbornene dicarboxylic acid anhydride. In other words, methylnorbornene dicarboxylic acid anhydride is produced by Diels-Alder reaction of the hydrocarbon fraction containing 1 mol of MCPD components with 0.7–1.0 mol of maleic anhydride which is performed at 0°-50° C. for 10 minutes to 10 hours in the presence of a protonic acid catalyst.

According to the process of the present invention, methylnorbornene dicarboxylic acid anhydride is produced in the presence of a protonic acid. The protonic acid functions as an isomerization catalyst for 5-MCPD. In other words, it isomerizes 5-MCPD into 1-MCPD and/or 2-MCPD and subjects them to Diels-Alder reaction. This isomerization is necessary because the hydrocarbon fraction as a raw material for the process of the present invention contains 5-MCPD, which does not react with maleic anhydride at low temperatures on account of its steric hindrance as mentioned above.

Therefore, the process of the present invention is capable of converting all of 5-MCPD in the hydrocarbon fraction into methylnorbornene dicarboxylic acid anhydride even though the reaction temperature is low.

The protonic acid may be selected from aromatic sulfonic acids (such as benzenesulfonic acid, p-toluenesulfonic acid, and p-xylene-2-sulfonic acid), mineral acids (such as sulfuric acid, phosphoric acid, and hydrochloric acid), and heteropolyacids (such as phosphomolybdic acid, phosphotungstic acid, silicomolybdic acid, and silicotungstic acid), the most desirable of which are aromatic sulfonic acids having substituent $C_1$ or $C_2$ alkyl groups on the aromatic ring (such as benzenesulfonic acid, p-toluenesulfonic acid, and p-xylene-2-sulfonic acid).

The protonic acid should be used in an amount of 0.01–5 wt. %, preferably 0.05–3 wt. %, based on the amount of 5-MCPD.

The process of the present invention for producing methylnorbornene dicarboxylic acid anhydride may be carried out either continuously or batchwise at a reaction temperature of 0°–50° C., preferably 20°–40° C. If the reaction temperature is below 0° C., the isomerization of 5-MCPD will be slow. If the reaction temperature is above 50° C., other diolefin components than MCPD will come in the reaction, giving rise to more heavy substances. The reaction time for batchwise operation should be 10 minutes to 10 hours, preferably 30 minutes to 3 hours.

It is desirable to carry out the isomerization reaction and Diels-Alder reaction simultaneously in the presence of a protonic acid catalyst. If the two reactions are performed sequentially (that is, isomerization of 5-MCPD contained in the hydrocarbon fraction is performed first in the presence of a protonic acid catalyst and subsequently Diels-Alder reaction for maliec anhydride is performed), the isomerization of 5-MCPD is slow and 1-MCPD and 2-MCPD (which are originally present or derived by isomerization) undergo dimerization.

The present invention provides a process for producing methylnorbornene dicarboxylic acid anhydride economically from a $C_{6-7}$ hydrocarbon fraction containing diolefins which is a steam cracking product, in place of expensive methylcyclopentadiene dimer.

In addition, the process of the present invention gives rise to methylnorbornene dicarboxylic acid anhydride of high purity in high yields because it resorts to the reaction which is performed at low temperatures in the presence of a protonic acid.

The invention will be described in more detail with reference to the following examples, which are not intended to restrict the scope of the invention. In the examples, "%" means "% by weight" unless otherwise indicated.

EXAMPLE 1

In a 3-liter four-mouth flask equipped with a reflux condenser and stirrer were placed 119.4 g of maleic anhydride (which is equimolar with MCPD in 1500 q of the raw material (1) shown below) and p-toluenesulfonic acid (made by Tokyo Kasei) in an amount equivalent to 0.5% of 5-MCPD. With the contents kept at 35° C., 1500 g of the raw material (1) shown below was added dropwise over 30 minutes. Then, the contents were kept at the same temperature for 1 hour to perform Diels-Alder reaction.

Analysis of the reaction product by gas chromatography indicated that the conversion of MCPD was 100%. On distillation of the reaction product to remove unreacted components and to separate dicarboxylic acid anhydride, there were obtained 214.4 g of light yellowish liquid (distillate) and 9.0 g of residues. The amount of the distillate corresponds to 98.9 mol% based on MCPD. Analysis by gas chromatography indicated that the content of methylnorbornene dicarboxylic acid anhydride in the distillate was 97.8%.

| Composition of raw material (1) | |
|---|---|
| 1-MCPD | 1.4% |
| 2-MCPD | 2.0% |
| 5-MCPD | 3.1% |
| 1,3-cyclohexadiene | 1.0% |
| 1,3-hexadiene | 0.2% |
| 2-ethyl-1,3-butadiene | 0.5% |
| Benzene | 60.0% |
| Toluene | 25.0% |
| $C_{6-7}$ olefin, paraffin | 6.8% |

EXAMPLE 2

Diels-Alder reaction was carried out in the same manner as in Example 1 except that p-toluenesulfonic acid was replaced by benzenesulfonic acid (made by Tokyo Kasei). Analysis of the reaction product by gas chromatography indicated that the conversion of MCPD was 100%. On distillation of the reaction product to remove unreacted components and to separate dicarboxylic acid anhydride, there were obtained 216.3 g of light yellowish liquid (distillate) and 9.2 g of residues. The amount of the distillate corresponds to 99.7 mol% based on MCPD. Analysis by gas chromatography indicated that the content of methylnorbornene dicarboxylic acid anhydride in the distillate was 97.1%.

EXAMPLE 3

Diels-Alder reaction was carried out in the same manner as in Example 1 except that p-toluenesulfonic acid was replaced by p-xylene-2-sulfonic acid (made by Tokyo Kasei). Analysis of the reaction product by gas chromatography indicated that the conversion of MCPD was 98.1%. On distillation of the reaction product to remove unreacted components and to separate dicarboxylic acid anhydride, there were obtained 208.5 g of light yellowish liquid (distillate) and 8.5 g of residues. The amount of the distillate corresponds to 96.1 mol% based on MCPD. Analysis by gas chromatography indicated that the content of methylnorbornene dicarboxylic acid anhydride in the distillate was 97.9%.

EXAMPLE 4

Diels-Alder reaction was carried out in the same manner as in Example 1 except that p-toluenesulfonic acid was replaced by 85% aqueous solution of phosphoric acid (made by Koso Kagaku) in an amount equivalent to 0.1% of 5-MCPD and the reaction temperature was changed to 20° C. Analysis of the reaction product by gas chromatography indicated that the conversion of MCPD was 100%. On distillation of the reaction product to remove unreacted components and to separate dicarboxylic acid anhydride, there were obtained 215.0 g of light yellowish liquid (distillate) and 12.7 g of residues. The amount of the distillate corresponds to 99.1 mol based on MCPD. Analysis by gas chromatography indicated that the content of methylnorbornene dicarboxylic acid anhydride in the distillate was 95.3%.

COMPARATIVE EXAMPLE 1

Diels-Alder reaction was carried out in the same manner as in Example 1 except that p-toluenesulfonic acid was replaced by boron trifluoride-ethyl ether complex (made by Koso Kagaku) in an amount equivalent to 0.1% of 5-MCPD and the reaction temperature was changed to 20° C. Analysis of the reaction product by gas chromatography indicated that the conversion of MCPD was 100%. On distillation of the reaction product to remove unreacted components and to separate dicarboxylic acid anhydride, there were obtained 210.3 g of light yellowish liquid (distillate) and 23.9 g of residues. The amount of the distillate corresponds to 89.8 mol% based on MCPD. Analysis by gas chromatography indicated that the content of methylnorbornene dicarboxylic acid anhydride in the distillate was 82.5%.

The catalyst based on this comparative example, $BF_3$-ethyl ether complex, is considered the next best catalyst as compared with the protonic acid catalyst of this invention.

EXAMPLES 5 TO 10 AND COMPARATIVE EXAMPLE 2 AND 3

Diels-Alder reaction was carried out in the same manner as in Example 1 except that change was made in the kind and amount of the protonic acid catalyst and the reaction temperature as shown in Table 1. The amount of the protonic acid catalyst is expressed in terms of wt. % based on 5-MCPD.

The conversion of MCPD determined by gas chromatography, the amount of dicarboxylic acid anhydride in the distillate and the amount of distillation residues, and the content of methylnorbornene dicarboxylic acid anhydride in the distillate determined by gas chromatography are also shown in Table 1.

5-MCPD was 100%. On distillation of the reaction product to remove unreacted components and to separate dicarboxylic acid anhydride, there were obtained 104.5 g of light yellowish liquid (distillate) and 3.2 g of residues. The amount of the distillate corresponds to 97.7 mol% based on 5-MCPD. Analysis by gas chromatography indicated that the content of methylnorbornene dicarboxylic acid anhydride in the distillate was 96.9%.

| Composition of raw material (2) | |
|---|---|
| 5-MCPD | 3.2% |
| 1,3-cyclohexadiene | 1.1% |
| 1,3-hexadiene | 0.2% |
| 2-ethyl-1,3-butadiene | 0.5% |
| Benzene | 61.0% |
| Toluene | 26.0% |
| $C_{6-7}$ olefin, paraffin | 8.0% |

What is claimed is:

1. A process for producing methylnorborene dicarboxylic anhydride by reacting a $C_6$-$C_7$ fraction which results from steam cracking of a hydrocarbon mixture, said $C_6$-$C_7$ fraction containing 5-methylcyclopentadiene with maleic anhydride at a temperature of 0°–50° C. in the presence of protonic acid whereby the 5-methylcyclopentadiene is isomerized to 1-methylcyclopentadiene and 2-methylcyclopentadiene or mixtures thereof.

2. The process of claim 1 wherein said protonic acid is an aromatic sulfonic acid having a $C_1$ or $C_2$ alkyl substituent on the aromatic ring.

3. The process of claim 1 wherein said $C_6$-$C_7$ fraction comprises about 0.7–2.0 wt. % 1-methylcyclopentadiene, 0.8–2.0 wt. % 2-methylcyclopentadiene, 1.5–1.0 wt. % 5-methylcyclopentadiene, 0.5–1.0 wt. % 1,3-cyclohexadiene, 0.2–1.0 wt. % 1,3-hexadiene, 0.3–1.0 wt. % 2-ethyl-1,3-butadiene, 4.5–8.5 wt. % C6-C7 olefins and paraffin, 45–60 wt. % benzene, and 20–40 wt. % toluene.

4. The process of claim 1 wherein there is present about 0.01–5 wt. % of said protonic acid, based on the amount of 5-methylcyclopentadiene.

5. The process of claim 1 wherein there is present 0.7–1.0 mol of maleic anhydride per mol of methylcyclopentadiene isomers.

TABLE 1

| Example No. | Catalyst Kind | Amount (%) | Reaction temperature (°C.) | Conversion of MCPD (%) | Dicarboxylic acid anhydride Yield (g) | Dicarboxylic acid anhydride Mol % (on MCPD) | Distillation residue yield (g) | Content of methyl-norbornene dicarboxylic acid anhydride (%) |
|---|---|---|---|---|---|---|---|---|
| Example 5 | p-Toluenesulfonic acid | 0.1 | 35 | 95.2 | 202.8 | 93.5 | 7.8 | 98.2 |
| Example 6 | p-Toluenesulfonic acid | 2.5 | 35 | 100 | 215.2 | 99.2 | 10.3 | 97.2 |
| Example 7 | p-Toluenesulfonic acid | 0.5 | 20 | 97.5 | 210.8 | 97.2 | 7.0 | 98.4 |
| Example 8 | p-Toluenesulfonic acid | 0.5 | 50 | 100 | 211.9 | 97.7 | 15.8 | 96.8 |
| Example 9 | Sulfuric acid | 0.1 | 20 | 100 | 214.0 | 98.7 | 18.1 | 93.7 |
| Example 10 | 12-Tungstophosphoric acid | 0.1 | 20 | 100 | 213.3 | 98.4 | 16.6 | 94.1 |
| Comparative Example 2 | p-toluenesulfonic acid | 0.1 | 80 | 100 | 201.2 | 92.8 | 24.2 | 84.2 |
| Comparative Example 3 | None | — | 35 | 58.4 | 125.5 | 57.9 | 4.8 | 87.3 |

EXAMPLE 11

Diels-Alder reaction was carried out in the same manner as in Example 1 except that the amount of maleic anhydride was changed to 58.9 g, which is equimolar with 5-MCPD contained in 1500 g of the raw material (2) shown below. Analysis of the reaction product by gas chromatography indicated that the conversion of